United States Patent [19]

Georgiev et al.

[11] Patent Number: 4,692,515
[45] Date of Patent: Sep. 8, 1987

[54] ADAMANTANE-SPIROLACTAMS

[75] Inventors: Vassil S. Georgiev, Rochester; George B. Mullen, Avon, both of N.Y.

[73] Assignee: Pennwalt Corporation, Philadelphia, Pa.

[21] Appl. No.: 874,917

[22] Filed: Jun. 16, 1986

Related U.S. Application Data

[63] Continuation-in-part of Ser. No. 653,632, Sep. 24, 1984, abandoned.

[51] Int. Cl.$^4$ .................. C07D 205/12; A61K 31/395
[52] U.S. Cl. .................................... 540/203; 568/818; 585/352; 585/931
[58] Field of Search .......................................... 540/203

[56] References Cited

PUBLICATIONS

Sasaki, Chem Abs 73, 97818n (1973).

Primary Examiner—Mark L. Berch

[57] ABSTRACT

Biologically active substituted spiro[azetidin-2-one-4,2'(or 3,2')adamantanes] of the formula

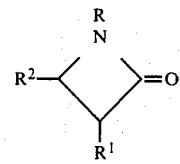

where R is hydrogen, —SO$_2$Cl, or alkyl, and one of R$^1$ and R$^2$ is an adamantyl group which shares a ring carbon with the lactam group and the other is alkyl, substituted alkyl, phenyl, or substituted phenyl, are disclosed herein.

16 Claims, No Drawings 4,692,515

ADAMANTANE-SPIROLACTAMS

RELATED APPLICATIONS

This application is a continuation-in-part of copending application Ser. No. 653,632, filed Sept. 24, 1984 now abandoned.

FIELD OF THE INVENTION

This invention relates to new substituted spiro[azetidin-2-one-4,2'(or 3,2')adamantanes]. More particularly, it relates to 3(or 4-)-substituted spiro[azetidin-2-one-4,2'(or 3,2')tricyclo[3.3.1.1.$^{3,7}$]decanes] having various substituent groups. Derivatives of this type have demonstrated, in test procedures, one or more utilities including antimicrobial activity against Neisseria gonorrhoeae, Streptococcus aureus and Streptococcus pneumoniae, and anticonvulsant, antihypoxia, antiparkinson and anticholinergic activity.

STATEMENT OF THE INVENTION

This invention is a compound comprising a substituted spiro[azetidin-2-one-4,2'(or 3,2')adamantane] of the structure:

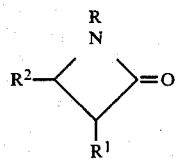

where R is hydrogen, —SO$_2$Cl, or alkyl and one of R$^1$ and R$^2$ is an adamantyl group which shares a ring carbon with the lactam group and the other is alkyl, substituted alkyl, phenyl, or substituted phenyl.

DETAILED DESCRIPTION OF THE INVENTION

The compounds of this invention are spiro[azetidin-2-one-4,2'(or 3,2')-tricyclo[3.3.1.1$^{3,7}$]decane] derivatives wherein the substituent groups as shown in the above structural formula are R, R$^1$ and R$^2$ defined as follows:

R is the substituent group of the nitrogen atom in the ring structure and is either hydrogen, —SO$_2$Cl or C$_1$–C$_8$ alkyl. Preferably, R is either hydrogen, a lower alkyl having less than four carbons, or —SO$_2$Cl.

One of R$^1$ and R$^2$ is an adamantyl group which shares a ring carbon with the indicated ring carbon of the lactam moiety and the other is either C$_1$–C$_8$ alkyl, substituted C$_1$–C$_8$ alkyl, phenyl or substituted phenyl. The alkyl substituent group for R–R$^2$ may have up to 8 carbon atoms including, for example, methyl, ethyl, propyl, isopropyl, isobutyl, butyl, pentyl, isopentyl, hexyl, octyl, and isooctyl. The attachment of the adamantyl group through R$^1$ or R$^2$ is demonstrated in the structures set forth below:

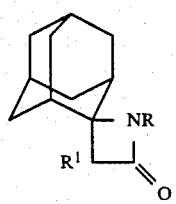

I.

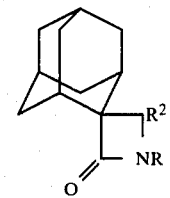

II.

It is preferred that one of R$^1$ and R$^2$ comprise a phenyl radical that may be also substituted with haloalkyl, alkoxy or formyl radicals, or an alkyl having less than four carbon atoms.

In general, the derivatives of this invention are prepared by the Grignard reaction of 2-adamantanone or its oxirane homolog with an appropriate organomagnesium halide to provide the corresponding 2-alkyltricyclo[3.3.1.1$^{3,7}$]decan-2-ol. Dehydration of the resulting decanol compound forms the corresponding methylene analog which, in turn, when subjected to cycloaddition with chlorosulfonyl isocyanate, provides the N-chlorosulfonyl adamantane-spiroazetidin-2-one. Reductive dechlorosulfonation of the spiroazetidinone furnishes the corresponding beta-lactam analog.

Alternatively, the compounds of this invention may be prepared by the treatment of N-substituted adamantyl nitrone with an alkyl crotonate to produce the spiro[isoxazolidine-3,2'-tricyclo[3.3.1.1$^{3,7}$]decane]ester. Catalytic hydrogenation of the latter results in a ring-opening to provide the aminoalcohol ester. Subsequent treatment of the aminoalcohol ester with an alkylmagnesium halide furnishes the 1-alkyl-3-(α-hydroxyalkyl)-spiro[azetidin-2-one-4,2'tricyclo[3.3.1.1$^{3,7}$]decane].

EXAMPLES

The following examples are set forth to demonstrate the preparation of representative compounds of this invention.

EXAMPLE 1

1-Chlorosulfonyl-3-phenyl-spiro[azetidin-2-one-4,2'-tricyclo[3.3.1.1$^{3,7}$]decane] (Compound A) was prepared by first synthesizing 2-(phenylmethyl)-tricyclo[3.3.1.1$^{3,7}$]decan-2-ol and dehydrating this decanol compound to form 2-(phenylmethylene)-tricyclo[3.3.1.$^{3,7}$]decane in accordance with the following procedure:

Benzylmagnesium chloride was prepared by reacting benzyl chloride (37.0 ml, 0.320 mol) with magnesium turnings (8.50 g, 0.350 mol) in 125 ml anhydrous ether (under N$_2$). Then, a solution of 2-adamantanone (24.03 g, 0.160 mol) in 250 ml anhydrous ether was added gradually over a period of 60 minutes. The resulting suspension was stirred at room temperature for 18 hours, and then quenched by cautious addition of 250 ml 2N hydrochloric acid. The organic layer was separated, washed with water, then dried over MgSO$_4$, and the solvent evaporated leaving, after crystallization from pentane, 32.47 g (84%) of 2-(phenylmethyl)-tricyclo[3.3.1.1$^{3,7}$]-decan-2-ol. Mp 58°–60° C. The decanol compound was then dehydrated using the method of Keul[1] to produce 2-(phenyl-methylene)-tricyclo[3.3.1.1$^{3,7}$]decane. The dehydration procedure was as follows:

A solution of the above identified decanol compound and p-toluenesulfonic acid monohydrate (molar ratio of 10/1) in toluene was refluxed for 1 hour (with separation of water), cooled to ambient temperature and washed sequentially with water and saturated aqueous sodium chloride. The solvent (toluene) was then evaporated to provide the methylene precursor of Compound A.

1. H. Keul, Chem. Ber. 108 (1975).

Under a nitrogen atmosphere, a solution of 24.5 g (0.109 mol) of 2-(phenylmethylene)-tricyclo[3.3.1.1$^{3,7}$]-decane in 75 ml ether was added dropwise over a 20 minute period to an ice-cold solution of 15.0 ml (0.172 mol) of chlorosulfonyl isocyanate in 250 ml ether. The reaction mixture was stirred in an ice bath for 8 hours, then at room temperature for 90 hours. After the addition of pentane, the resulting precipitate was filtered off. 21.5 g (68%) of 1-chlorosulfonyl-3-phenyl-spiro[azetidin-2-one-4,2'-tricyclo[3.3.1.1$^{3,7}$]decane] was obtained, melting at 96°–101° C.

EXAMPLE 2

1-Chlorosulfonyl-3-[p-(bromomethyl)phenyl]-spiro[azetidin-2-one-4,2'-tricyclo[3.3.1.1$^{3,7}$]decane (Compound B) and 1-chlorosulfonyl-4-[p-methoxyphenyl]-spiro[azetidin-2-one-3,2'-tricyclo[3.3.1.1$^{3,7}$]decane (Compound C) were also prepared according to the procedure of Example 1 from the methylene precursors of the corresponding derivative products which precursors were prepared as follows:

The 2-[[p-(bromomethyl)phenyl]methylene]-tricyclo[3.3.1.1$^{3,7}$]decane (methylene precursor of Compound B) was prepared by first synthesizing 2-[(p-methylphenyl)methyl]-tricyclo[3.3.1.1$^{3,7}$]decan-2-ol from 2-adamantanone and p-methylbenzylmagnesium chloride and dehydrating the resulting decanol similarly as described above for 2-methyl-tricyclo[3.3.1.1$^{3,7}$]decan-2-ol to provide the 2-[(p-methylphenyl)methylene]-tricyclo[3.3.1.1$^{3,7}$]decane. A solution of 1.65 g. (6.9 mmol) of the latter product, 1.30 g. N-bromosuccinimide, and 0.09 g. of benzoyl peroxide in 20 ml carbon tetrachloride was refluxed for 4 hours, then cooled to room temperature and filtered. The filtrate was washed sequentially with 5% aqueous sodium bicarbonate and water, then dried over MgSO$_4$ and flash-chromatographed on silica gel using hexane-ethyl acetate (9.5:0.5) as the eluent. 1.42 g. (65%) of 2-[[(p-(bromomethyl)phenyl]methylene]-tricyclo[3.3.1.1$^{3,7}$]-decane was obtained, melting at 48°–52° C. (acetone).

The 2-[(p-methoxyphenyl)methylene]-tricyclo[3.3.1.1$^{3,7}$]decane (precursor of Compound C) was prepared by first synthesizing 2-[(p-methoxyphenyl)methyl]-tricyclo[3.3.1.1$^{3,7}$]decan-2-ol by the following procedure:

p-Methoxyphenylmagnesium bromide is prepared by reacting p-bromoanisole (14.2 ml, 0.11 mol) with magnesium turnings (2.70 g, 0.11 mol) in 80 ml anhydrous ether (under N$_2$). To this ether solution of Grignard reagent is added a solution of spiro[oxirane-2,2'-tricyclo[3.3.1.1$^{3,7}$]decane]$^2$ (17.4 g, 0.10 mol) in 100 ml anhydrous ether, maintained at 0° C., over a period of 40 minutes. The resulting suspension was stirred at room temperature for 2 hours and then quenched by slow addition of 150 ml 1N hydrochloric acid. The organic layer was dried over MgSO$_4$ and the solvent removed in vacuo yielding 27.2 g (100%) of 2-[(p-methoxyphenyl)methyl]-tricyclo[3.3.1.1$^{3,7}$]decan-2-ol as an oil which was flash-chromatographed on silica gel using hexane-ethyl acetate (3:1) as the eluent. The decanol compound was dehydrated similarly as described above to provide the methylene precursor of Compound C.

2. D. Farcasiu, Synthesis, 1972: 615.

EXAMPLE 3

3-Phenyl-spiro[azetidin-2-one-4,2'-tricyclo[3.3.1.1$^{3,7}$]decane] (Compound D) is prepared from Compound A (Example 1) by adding dropwise, over a period of 45 minutes, a 20% by weight aqueous solution of sodium sulfite (700 ml) to a solution of 16.95 g (0.0463 mol) of Compound A in 250 ml of tetrahydrofuran. During the addition, the pH of the reaction mixture was maintained at 7–8 by the dropwise addition of 200 ml of 10% by weight aqueous potassium hydroxide. The reaction mixture was stirred vigorously at ambient temperature for an additional 2 hours followed by the addition of ether. The organic layer was separated, dried over MgSO$_4$, and the solvent (ether-tetrahydrofuran) removed in vacuo to give 11.31 g (91%) of Compound D as a white solid. Mp. 218°–221° C. (ethyl acetate).

Anal. Calcd. for C$_{18}$H$_{21}$NO: C, 80.86; H, 7.92; N, 5.24. Found: C, 80.64; H, 8.18; N, 5.23.

Compound D demonstrated in later described test procedures, anticonvulsant, anticholinergic and antiparkinson activity, all at dosages of 400 mg/kg. Testing in vitro proved that this compound was inactive as a bactericide.

Compounds B and C were similarly treated as in Example 3 to provide the derivatives of Examples 4 and 5 below.

EXAMPLE 4

3-[p-(Bromomethyl)phenyl]-spiro[azetidin-2-one-4,2'-tricyclo[3.3.1.1$^{3,7}$]decane] (Compound E). Mp. 198°–200° C. (ethyl acetate).

Anal. Calcd. for C$_{19}$H$_{22}$BrNO: C, 63.34; H, 6.15; Br, 22.18; N, 3.89. Found: C, 63.06; H, 6.12; Br, 22.55; N, 3.53.

Compound E demonstrated antiparkinson activity at a dosage of 400 mg/kg in a later described test procedure.

EXAMPLE 5

4-(p-Methoxyphenyl)-spiro[azetidin-2-one-3,2'-tricyclo[3.3.1.1$^{3,7}$]decane] (Compound F). Mp. 179°–180° C. (ethyl acetate).

Anal. Calcd. for C$_{19}$H$_{23}$NO$_2$: C, 76.74; H, 7.79; N, 4.71. Found: C, 76.82; H, 7.74; N, 4.55.

Compound F demonstrated antihypoxia activity at 100 mg/kg in a later described test procedure but proved inactive as a bactericide when tested in vitro.

EXAMPLE 6

3-(4-Formylphenyl)-spiro[azetidin-2-one-4,2'-tricyclo[3.3.1.1$^{3,7}$]decane] (Compound G) was prepared as follows:

3-[(p-Bromomethyl)phenyl]-spiro[azetidin-2-one-4,2'-tricyclo[3.3.1.1$^{3,7}$]decane] (Compound E) (4.63 g, 0.0128 mol) was added under nitrogen atmosphere to a suspension of 1.20 g sodium bicarbonate in 55 ml anhydrous dimethyl sulfoxide, and the reaction mixture was stirred at 120° C. for 4 hours. Following cooling to ambient temperature, the reaction mixture was poured into ice-water and extracted with chloroform. The organic extract was dried over sodium sulfate and the solvent removed in vacuo, followed by flash chromatography of the oily residue on silica gel using hexane-ethyl acetate (2:1) as the eluent. 1.16 g (31%) of pure derivative Compound G was obtained. Mp. 209°–212° C. (decomp).

Anal. Calcd. for $C_{18}H_{21}NO_2$: C, 77.28; H, 7.17; N, 4.74. Found: C, 76.84; H, 7.35; N, 4.67.

Compound G was tested in vitro only for antimicrobial activity and found inactive. It is anticipated that this compound will show antihypoxia, antiparkinson, anticonvulsant or antichlolinergic activity, if tested.

EXAMPLE 7

The compound 1-methyl-3-(α-hydroxyethyl)-spiro[azetidin-2-one-4,2'-tricyclo[3.3.1.1$^{3,7}$]decane] (Compound H) was prepared as follows:

Methyl 2,5-dimethyl-spiro[isoxazolidine-3,2'-tricyclo[3.3.1.1$^{3,7}$]decane]-4-carboxylate was first prepared by refluxing a solution of N-methyladamantyl nitrone [prepared by reacting 36.09 g (0.240 mol) 2-adamantanone, 20.63 g (0.247 mol) N-methylhydroxylamine hydrochloride and 20.79 g (0.247 mol) sodium bicarbonate in 600 ml ethanol] and methyl crotonate (50 ml, 2.0 equivalents) in 600 ml benzene for 20 hours. The dark-colored reaction mixture was cooled to room temperature, and then washed sequentially with water and a saturated aqueous solution of sodium chloride. After drying over $MgSO_4$, the solvent was removed in vacuo leaving, after recrystallization from methanol, 22.91 g (34%) of the methyl ester derivative. Mp. 123°–124° C.

Anal. Calcd. for $C_{16}H_{25}NO_3$: C, 68.79; H, 9.02; N, 5.01. Found: C, 69.06; H, 9.23; N, 4.98.

Methyl α-(1-hydroxyethyl)-2-(methylamino)tricyclo[3.3.1.1$^{3,7}$]decane-2-acetate (Compound I) was prepared by hydrogenating the above methyl ester derivative (9.99 g, 0.036 mol) in 200 ml glacial acetic acid over 1.06 g palladium-on-carbon in a Parr apparatus at 45 psi. After 28 hours, the reaction mixture was filtered through celite and the solvent removed in vacuo to yield 10.1 g (100%) of Compound I as a colorless oil. The corresponding hydrochloride salt of Compound I was crystallized from methanol and melted at 193°–198° C. (decomp).

Anal. Calcd. for $C_{16}H_{28}ClNO_3$: C, 60.46; H, 8.88; Cl, 11.15; N, 4.41. Found: C, 60.82; H, 8.71; Cl, 11.26; N, 4.36.

From Compound I, the 1-methyl-3-(α-hydroxyethyl)-spiro[azetidin-2-one-4,2'-tricyclo[3.3.1.1$^{3,7}$]decane] (Compound H) was synthesized as follows:

22 ml (4.0 equivalents) of 3N ethylmagnesium bromide in ether was added, at −20° C. and over a period of 35 minutes, to a solution of 4.68 g (0.0166 mol) of Compound I in 75 ml anhydrous tetrahydrofuran. A precipitate was formed during the addition. The reaction mixture was warmed to room temperature and stirred for an additional 4 hours, then cooled in an ice-bath and quenched cautiously with 50 ml saturated aqueous ammonium chloride. Following the addition of methylene chloride and water, the organic layer was washed sequentially with water and saturated aqueous sodium chloride, then dried ($MgSO_4$) and evaporated to leave, after recrystallization from ether-hexane, 1.36 g (33%) of Compound H. Mp. 131°–132° C.

Anal. Calcd. for $C_{15}H_{23}NO_2$: C, 72.25; H, 9.30; N, 5.62. Found: C, 72.42; H, 9.49; N, 5.58.

Compound H was found in a later described in vitro test procedure to have antibacterial activity against N. gonorrhoeae, S. aureus and S. pneumoniae at a dosage of 500 μg/per disc.

The following chart of the compounds of this invention is set forth to further identify the substituents and their positions relative to the azetidinone (lactam) portion of the molecule.

| Compound | Adamantane-spirolactam | | |
|---|---|---|---|
| | Structure | R Group | $R^1$ or $R^2$ Group |
| A | I | chlorosulfonyl | phenyl |
| B | I | chlorosulfonyl | p-(bromomethyl)phenyl |
| C | II | chlorosulfonyl | p-methoxyphenyl ($R^2$) |
| D | I | hydrogen | phenyl |
| E | I | hydrogen | p-(bromoethyl)phenyl |
| F | II | hydrogen | p-methoxyphenyl ($R^2$) |
| G | I | hydrogen | 4-formylphenyl |
| H | I | methyl | α-hydroxyethyl |

Test procedures for determining the utility of compounds of this invention are as follows:

Antihypoxia Activity

Groups of mice are tested at various times after the intraperitoneal administration of graded doses of the test compound. The animal's survival time in a hypoxic environment (96% nitrogen and 4% oxygen) is recorded. A statistical comparison (Wilcoxon rank sum) is made between coincident vehicle-treated animals and the experimental group. The dose-response, time course and minimum active dose (MAD) for a compound are obtained. Other modes of administration can also be used.

Antiparkinson Activity

This procedure is based on the ability of a test compound to prevent tremoring in mice induced by N-carbamoyl-2-(2,6-dichlorophenyl)acetamidine hydrochloride(LON 954).

(1) Procedure

Two groups of 5 mice each (fasted for 4 hours) are administered test compound (at ¼ of the LD50) or vehicle, intraperitoneally (i.p.). LON 954 (50 mg/kg) is administered orally (p.o.) 30 minutes later and the mice are housed individually in small plastic cubicles for observation. Aqueous solutions of LON 954 are subject to hydrolysis and should be made up when needed and used within one hour. The mice are observed for the occurrence and degree of tremor during a 15 minute period immediately following administration of LON 954.

(2) Evaluation of Data

The tremor produced by LON 954 (50 mg/kg p.o.) is both pronounced and continuous in control (untreated) mice.

Compounds which prevent tremoring in 3 or more mice are considered active.

Anticonvulsant Activity

This procedure is based on the ability of a test compound to block pentylenetetrazole-induced and electrical shock-induced convulsions in mice.

(1) Procedure

Two groups of 5 mice each are administered the test compound at ¼ of the LD50 or vehicle i.p. Thirty minutes later each mouse is administered pentylenetetrazole (PTZ), 150 mg/kg i.p. The mice are housed, by groups, in plastic cages. The animals are observed for 15 minutes immediately following PTZ administration. Alteration of the convulsive pattern such as delayed onset of convulsions, changes in the type of convulsions and prevention of convulsions are noted. The number of survivors 15 minutes after PTZ administration is recorded on the Data Sheet.

(2) Evaluation of Data

The dose of PTZ used as a convulsive challenge is higher than LD 100, therefore, the number of surviving mice 15 minutes post-PTZ can be used as an index of anticonvulsive activity. Active compounds are considered as those that protect 3 or more mice. Most compounds which afford protection against death also delay and moderate or prevent PTZ-induced seizures. The seizure pattern in untreated (control) mice is: (1) initial twitching, (2) a more severe generalized jerking of the body usually accompanied by a squeak which is followed immediately by (3) frank clonic convulsions which lead to tonic convulsions with tonic extension of the hind limbs.

Antibacterial Activity

The candidate compound is tested in vitro in a broth dilution test (homogenized) or a disc diffusion test as described, for example, in "Antibiotics in Laboratory Medicine", Ed. Victor Lorian, M.D., Williams and Wilkins, 1980.

Appropriate calibration with known agents permits the quantitative calculation of the minimal inhibitory concentration (MIC, expressed in micrograms per milliliter) causing complete inhibition of growth for the test compound. Compounds of this invention found to be active may be useful for the treatment or prevention of bacterial infection in warm-blooded animals and for the treatment of materials subject to bacterial contamination or deterioration.

For pharmaceutical purposes, the compounds of this invention can be administered to warm-blooded animals perorally or parenterally as active ingredients in customary dosage unit compositions. These compositions consist essentially of a dosage unit form containing the active ingredient and at least one inert pharmaceutical carrier. Dosage unit forms contemplated by the present invention include tablets, capsules, solutions, suspensions, lozenges, coated pills and parenteral compositions such as intramuscular, intravenous or intradermal preparations. Sustained release dosage forms are also contemplated where the active ingredient is bound to an ion exchange resin which, optionally, can be coated with a diffusion barrier coating to modify the release properties of the resin.

The quantity of active ingredient administered in such dosage forms can vary over a wide range depending upon the mode of administration, the size and weight of the patient and whether the nature of the treatment is prophylactic or therapeutic in nature. In general, dosage unit forms contain from about 500 mg to 3 g of the active ingredient, and in man, the dose is administered from 1 to 4 times daily. The total daily dosage will be from about 500 mg to 12 g, although lower and higher amounts can be used. A preferred total daily dose would be from 2 g to 10 g of active ingredient.

Pharmaceutical carriers or excipients used in the preparation of pharmaceutical compositions may be either organic or inorganic, solid or liquid in nature. Suitable solid excipients include gelatin, microcrystalline cellulose, lactose, starches and magnesium stearate. Suitable liquid excipients include water and alcohols such as ethanol, benzyl alcohol and poly(ethylene glycols). In general, the preferred liquid excipients particularly useful for injectable preparations include water, saline solution, dextrose solution and glycol solutions such as aqueous propylene glycol or aqueous poly(ethylene glycol). The properties of the formulations may be enhanced by the addition of one or more adjuvants possessing properties as viscosity enhancers, surfactants, pH modifiers, preservatives, sweeteners, stability enhancers, coloring agents, disintegration modifiers, propellants, emulsifying agents and humectants.

We claim:

1. A spiro[azetidin-2-one-4,2'(or 3,2')adamantane] compound having the following structure:

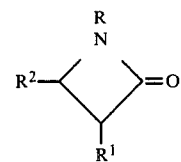

where R is hydrogen, $-SO_2Cl$, or an alkyl group and one of $R^1$ and $R^2$ is an adamantyl group which shares a ring carbon with the lactam moiety and the other is an alkyl, a hydroxy substituted alkyl, a phenyl, or a phenyl group substituted with a haloalkyl, alkoxy or formyl radical, said alkyl groups having from 1 to 8 carbon atoms.

2. The compound of claim 1 wherein $R^2$ represents the adamantyl group.

3. The compound of claim 2 wherein R is chlorosulfonyl.

4. The compound of claim 3 wherein $R^1$ is phenyl.

5. The compound of claim 3 wherein $R^1$ is p-(bromomethyl)phenyl.

6. The compound of claim 2 wherein R is hydrogen.

7. The compound of claim 6 wherein $R^1$ is phenyl.

8. The compound of claim 6 wherein $R^1$ is p-(bromomethyl)phenyl.

9. The compound of claim 6 wherein $R^1$ is 4-formylphenyl.

10. The compound of claim 2 wherein R is an alkyl group having less than 4 carbon atoms.

11. The compound of claim 10 wherein $R^1$ is α-hydroxyethyl.

12. The compound of claim 1 wherein $R^1$ represents the adamantyl group.

13. The compound of claim 12 wherein R is chlorosulfonyl.

14. The compound of claim 13 wherein $R^2$ is p-methoxyphenyl.

15. The compound of claim 12 wherein R is hydrogen.

16. The compound of claim 15 wherein $R^2$ is p-methoxyphenyl.

* * * * *